US00PP22101P3

(12) United States Plant Patent

Wu et al.

(10) Patent No.: US PP22,101 P3

(45) Date of Patent: Aug. 30, 2011

(54) FORAGE BERMUDAGRASS PLANT NAMED 'GOODWELL'

(50) Latin Name: *Cynodon dactylon (L.) Pers*
Varietal Denomination: GOODWELL

(75) Inventors: Yanqi Wu, Stillwater, OK (US); Charles M. Taliaferro, Stillwater, OK (US); Rick Kochenower, Guymon, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 49 days.

(21) Appl. No.: 12/050,292

(22) Filed: Mar. 18, 2008

(65) Prior Publication Data

US 2009/0007299 A1 Jan. 1, 2009

Related U.S. Application Data

(60) Provisional application No. 60/946,516, filed on Jun. 27, 2007.

(51) Int. Cl.
*A01H 5/00* (2006.01)

(52) U.S. Cl. ..... Plt./389

(58) Field of Classification Search ..... Plt./389
See application file for complete search history.

(56) References Cited

U.S. PATENT DOCUMENTS

PP16,801 P2 7/2006 Taliaferro et al.

OTHER PUBLICATIONS

Applicant's experimental use/testing and the experimental use of a third party under confidentiality agreement during 1995 and following years in Oklahoma and Kansas.

*Primary Examiner* — Kent L Bell

(74) *Attorney, Agent, or Firm* — Fellers, Snider, Blankenship, Bailey & Tippens, P.C.

(57) ABSTRACT

'Goodwell' is a hybrid forage bermudagrass. It has larger stems and wider leaves, and produces a more dense sod compared to "hay type" varieties. The stem size and leaf width is much greater compared to "grazing type" varieties while the sod density is somewhat less compared to the grazing type varieties.

7 Drawing Sheets

Latin name: *Cynodon dactylon* (L.) Pers.
Variety denomination: 'GOODWELL'.

BACKGROUND

'GOODWELL' is a new forage bermudagrass.

'GOODWELL' is an $F_1$ hybrid from the cross 74X 12-11×74X 12-12, made in 1984. The 74X 12-11 and 74X 12-12 parents were $F_1$ hybrids from the crosses A9959×SS-28 and SS-16×Colorado, respectively. The SS-28 and SS-16 parents were $F_1$ hybrids from the crosses S-16×A9945 and S-16×9958, respectively. The S-16 parent was an $F_1$ hybrid from the cross A8800×A10421. A9945 (PI 206427), A9958 (PI 251809), A9959 (PI 253302), Colorado, and A8800 (PI 269370) are clonal accessions from Turkey, Italy, Yugoslavia, Colorado, and Afghanistan, respectively. Several hundred $F_1$ hybrid plants from many crosses, including 74X 12-11×74X 12-12, were initially screened in a planting during the period 1985 through 1987. The 'GOODWELL' hybrid was one of several plants selected for further evaluation.

SUMMARY OF THE INVENTION

'GOODWELL' is an asexually reproducing forage bermudagrass. It has been evaluated for forage yield in several trials, performing favorably relative to standard varieties. Data from field trials and observational plantings indicate 'GOODWELL' to be well-adapted to production under irrigation in the Oklahoma panhandle and adjacent areas of the High Plains. Accordingly, the targeted use of the variety is in this region under irrigation. 'GOODWELL' has generally initiated spring growth slightly earlier than other common varieties, suggesting an edge in winter hardiness. 'GOODWELL' also exhibits larger stems and wider leaves compared to other commercial available varieties. 'GOODWELL' exhibits greater sod density that "hay type" varieties and taller growth than "grazing type" varieties. These are favorable characteristics for certain situations.

DETAILED BOTANICAL DESCRIPTION

Figure 1:
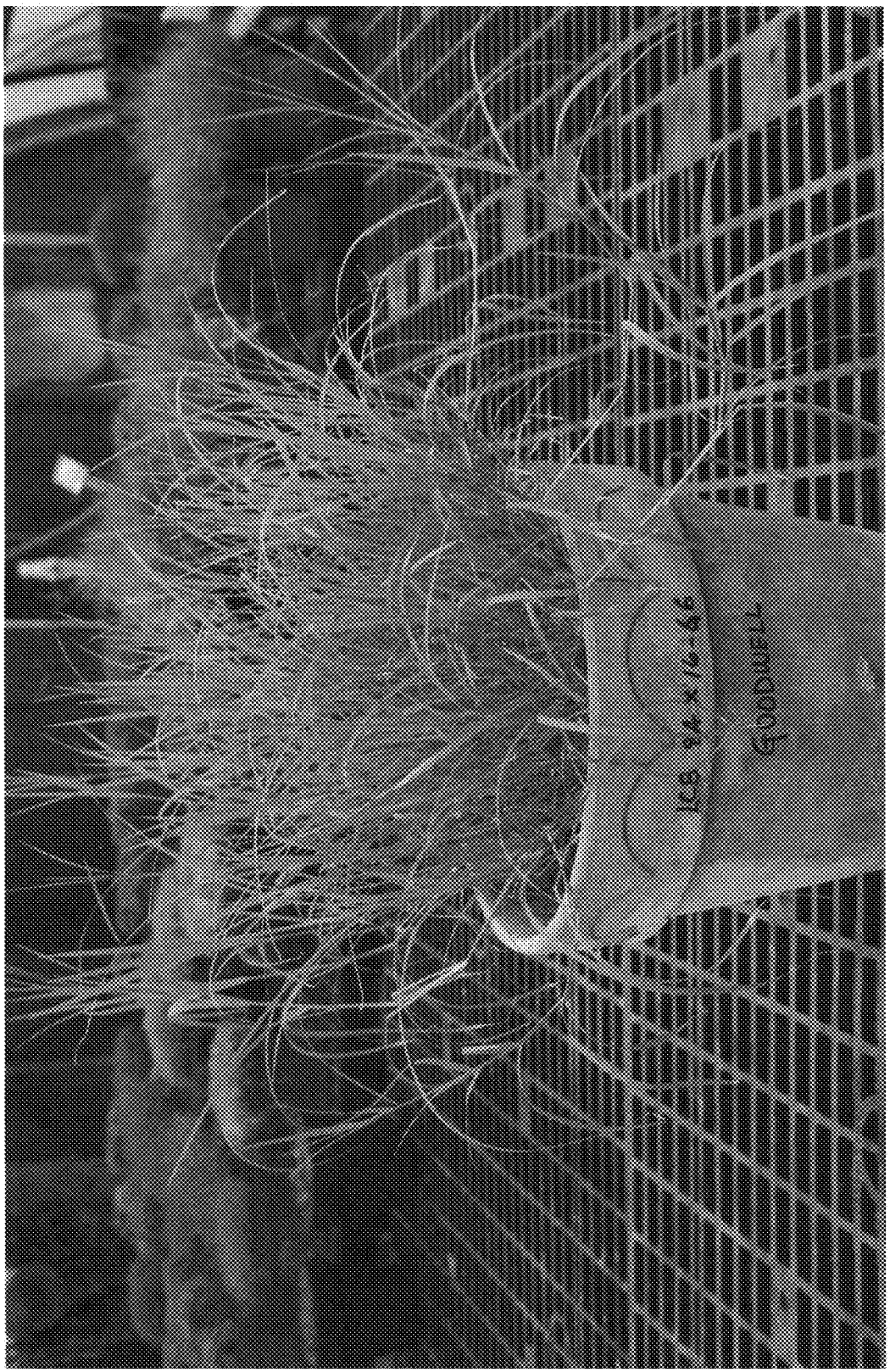
FIG. 1 is a photograph of a 9-10 week old growth of 'GOODWELL'.

'GOODWELL', a bermudagrass, *Cynodon dactylon* (L.) Pers. (LCB 84X 16-66) is an $F_1$ hybrid from the cross 74X 12-11×74X 12-12, made in 1984. The 74X 12-11 and 74X 12-12 parents were $F_1$ hybrids from the crosses A9959×SS-28 and SS-16×Colorado, respectively. The SS-28 and SS-16 parents were $F_1$ hybrids from the crosses S-16×A9945 and S-16×9958, respectively. The S-16 parent was an $F_1$ hybrid from the cross A8800×A10421. A9945 (PI 206427), A9958 (PI 251809), A9959 (PI 253302), Colorado, and A8800 (PI 269370) are clonal accessions from Turkey, Italy, Yugoslavia, Colorado, and Afghanistan, respectively. Several hundred $F_1$ hybrid plants from many crosses, including 74X 12-11×74X 12-12, were initially screened in a planting during the period 1985 through 1987. The 'GOODWELL' hybrid was one of several plants selected for further evaluation.

'GOODWELL' has larger stems and wider leaves, and produces a more dense sod compared to "hay type" varieties like Midland, Midland 99, and Tifton 44, 'GOODWELL'. It is typically lower growing (less tall) as well. The stem size and leaf width of 'GOODWELL' is much greater compared to "grazing type" varieties like Greenfield and World Feeder. The height of 'GOODWELL' is typically greater, while the sod density is somewhat less compared to the grazing type varieties. 'GOODWELL' produces many large, fleshy rhizomes that contribute to lateral spread during establishment. Lateral spread is also achieved by growth of stolons.

'GOODWELL' is highly infertile, producing only very few seed when grown in the presence of an effective pollinator. Consequently, it must be propagated asexually. Chromosome number has not yet been determined. It is likely a tetraploid with 2n=4x=36 chromosomes.

'GOODWELL' is propagated by conventional sprigging. It produces vigorous underground rhizomes and crown buds that function as vegetative propagules. Though not evaluated in a controlled experiment, its establishment characteristics (sprig viability, rate-of-spread) appear to be at least as good, and possibly superior to those of Midland, Midland 99, and Tifton 44. It's rate-of-spread probably is not as rapid as some of the aggressive "common" type varieties like Greenfield and World Feeder. A sprig planting rate of 30 or more bushels/acre, combined with good weed control and fertility management is recommended to hasten establishment.

Biomass production has been evaluated in trials at Haskell, Okla., Chickasha, Okla., Goodwell, Okla., and Mound Valley, Kans. Biomass performance of 'GOODWELL' relative to standard varieties has been best in irrigated (~6 acre inches/month during growing season) tests at Goodwell, Okla. In Tests 97-1 and 2003-1 at Goodwell, LCB 84X 16-66 produced significantly ($P>0.05$) more biomass than all standard varieties except Ozark (Tables 1 and 2). In tests at Haskell [Test 98-1 (Table 3); Test 2001-1 (Table 4)] and Chickasha [Test 98-2 (Table 5); Test 2001-2 (Table 6)] LCB 84X 16-66 produced less biomass than the best hay type varieties (Midland 99, Ozark, Tifton 44), but more biomass than the grazing type varieties (e.g. Greenfield). At Mound Valley, Kans., its biomass yield was not significantly greater than the yields of Ozark and Hardie, but significantly greater than Tifton 44, Midland, Greenfield, and World Feeder (Table 7).

Near Infrared Reflectance Spectroscopy predicted values for neutral detergent fiber, acid detergent fiber, acid detergent lignin, crude protein and digestible dry matter for samples collected during 1986-87 suggest its nutritional value is at least equal to that of Tifton 44 and Midland (Table 8).

There have been no reports or observations of any unusual and/or severe insect or disease problems with 'GOODWELL'. Leaf disease on 'GOODWELL' has been minimal when other bermudagrass varieties showed severe infections. The principal leaf spotting disease of bermudagrass caused by *Bipolaris cynodontis* is a major cause of performance (stand and biomass) decline in humid environments.

'GOODWELL' has maintained good stands at all locations where it has been tested (Chickasha, Haskell, Goodwell, Stillwater, and Mound Valley, Kans.). These results indicate its good adaptation to at least the bermudagrass growing area north of central Oklahoma. The consistent good performance of 'GOODWELL' at Goodwell appears to be related, at least in part, to good freeze tolerance. It has showed no winter injury at Goodwell during the period 1998 through 2006. In the Goodwell tests, it has consistently been the earliest, or among the earliest, varieties to initiate spring growth. It also demonstrated excellent winter survival and spring greenup at Mound Valley, Kans.

'GOODWELL' was tested under pivot irrigation near Goodwell, Okla. for the past 3 years by a local farmer under a memorandum-of-agreement. An initial 60 acres was established in 2004 and the remaining 60 acres under the irrigation circle was established in 2005. Establishment was good for both plantings, but better for the 2004 planting compared to the 2005 planting. Stocker cattle grazed the initially established 60 acres during the 2005 growing season. The farmer reported the following: an initial stocking rate of 5.28 head/acre (317 animals on 60 acres); 100 animals weighed off at 95 days gained 1.78 lbs./day; season-long total gain from all animals ~53,000 pounds, with an average daily gain of ~1.5 pounds. Gains of stocker cattle grazing the 120 acres during the 2006 growing season were not good (<~0.5 lbs./day), though carrying capacity continued very high. Reasons for the poor performance in 2006 are unknown, but possible contributing factors were: 1) relatively poor quality of the stocker animals, and 2) excessive maturity of the bermudagrass and consequent low nutritional value.

The farmer has over-seeded the 'GOODWELL' with small grains each fall, beginning in fall 2004. This has been easily accomplished and highly successful. Growers of World Feeder bermudagrass in the same region have had difficulty interseeding cool-season species, apparently due to its greater sod density. The farmer highly values ability to easily interseed cool season species into 'GOODWELL'.

The farmer also grows cool-season perennial grasses (bromegrass, orchardgrass) under irrigation circles. He believes the warm-season bermudagrass enhances his stocker grazing forage system. Additionally, he believes that the bermudagrass offers significant opportunity as hay crop in the High Plains region under irrigation.

Data from field trials and observational plantings indicate 'GOODWELL' to be well-adapted to production under irrigation in the Oklahoma panhandle and adjacent areas of the High Plains. Accordingly, the targeted use of the variety is in this region under irrigation. It has produced lower biomass yields than Tifton 44 and Midland 99 in tests at Chickasha and Haskell. However, even in bermudagrass growing areas outside the High Plains, 'GOODWELL' may have some advantage over varieties like Midland, Midland 99, and Tifton 44 relative to faster establishment and a more dense sod that better resists weed encroachment.

For the High Plains region, the closest competitor of 'GOODWELL' among commercial bermudagrass varieties is Ozark. Both combine excellent winter hardiness and very high biomass production capability in this region. 'GOODWELL' has generally initiated spring growth slightly earlier than Ozark at Goodwell, suggesting an edge in winter hardiness. The greater sod density of 'GOODWELL' compared to Ozark may be desirable when used for grazing at high stocking levels (more resistant to trampling injury). Conversely, the generally taller growth of Ozark compared to 'GOODWELL' may make it more attractive to producers when the intended use is primarily or solely for hay production. The greater sod density of LCB 84X 16-66 compared to Ozark should also make it more resistant to weed encroachment.

Figure 2:
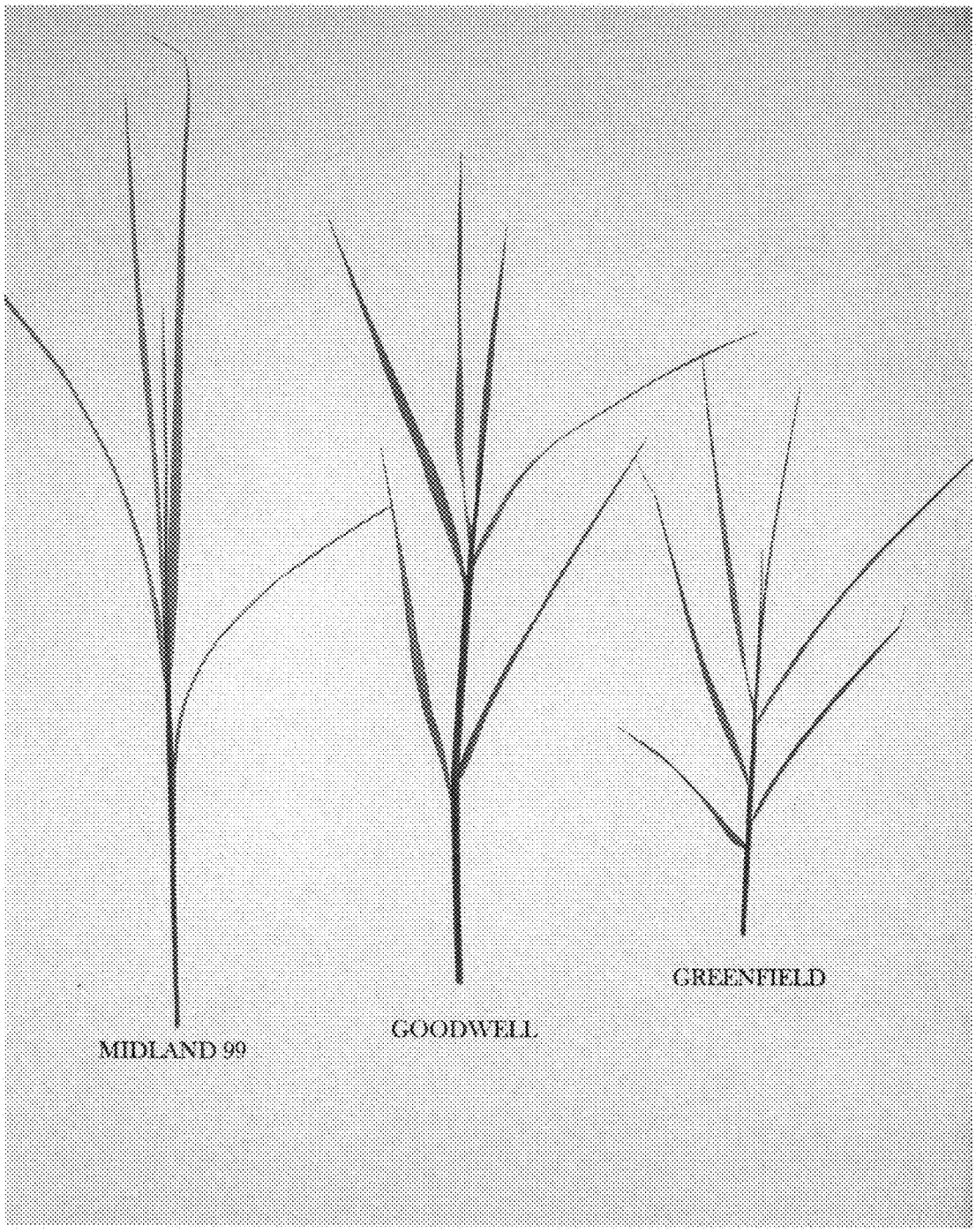
FIG. 2 is a comparative leaf image of MIDLAND 99 (left), 'GOODWELL' (center), and GREENFIELD (right) varieties.
Figure 3:
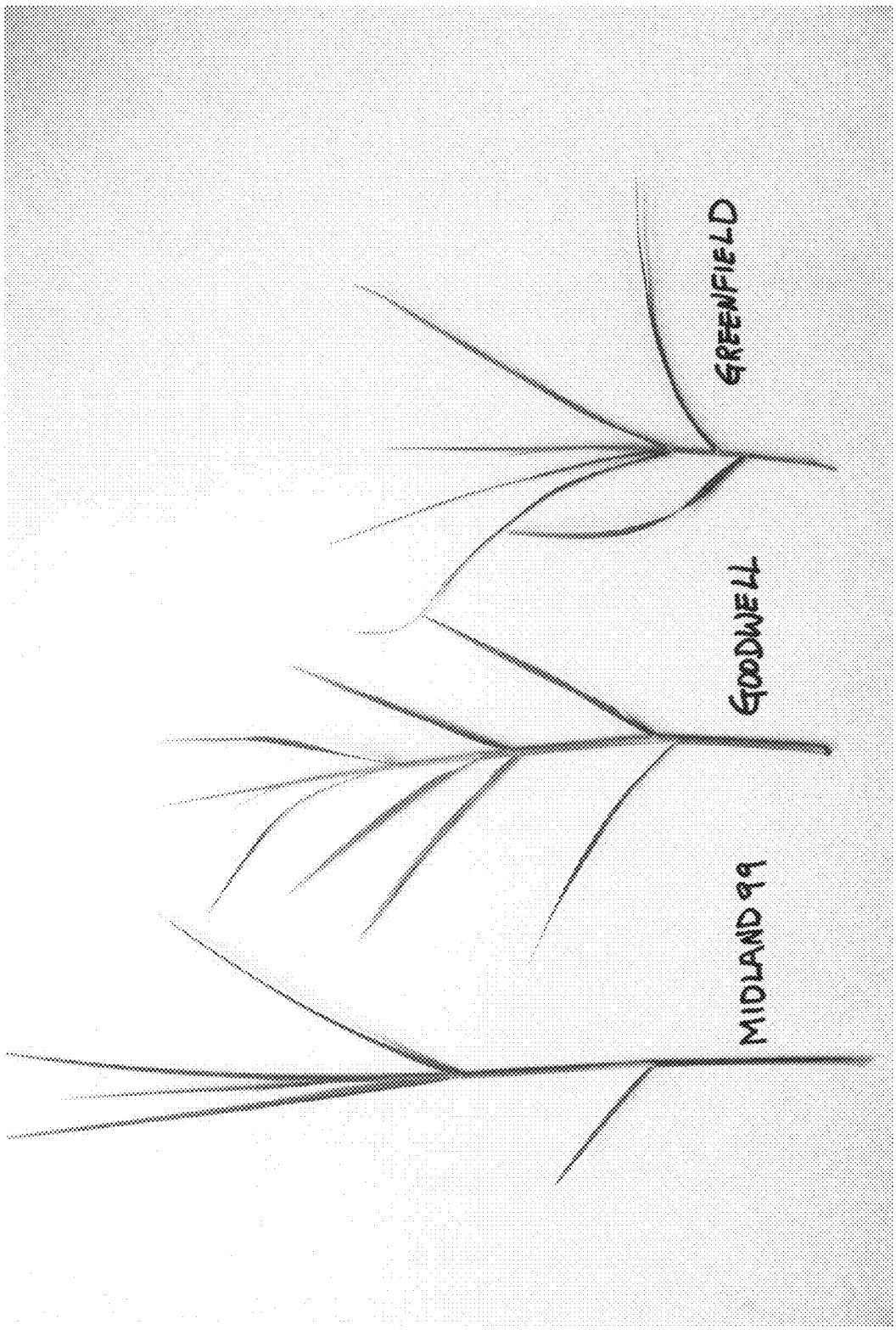
FIG. 3 is another comparative leaf image of MIDLAND 99 (left), 'GOODWELL' (center), and GREENFIELD (right) varieties.
Figure 4:
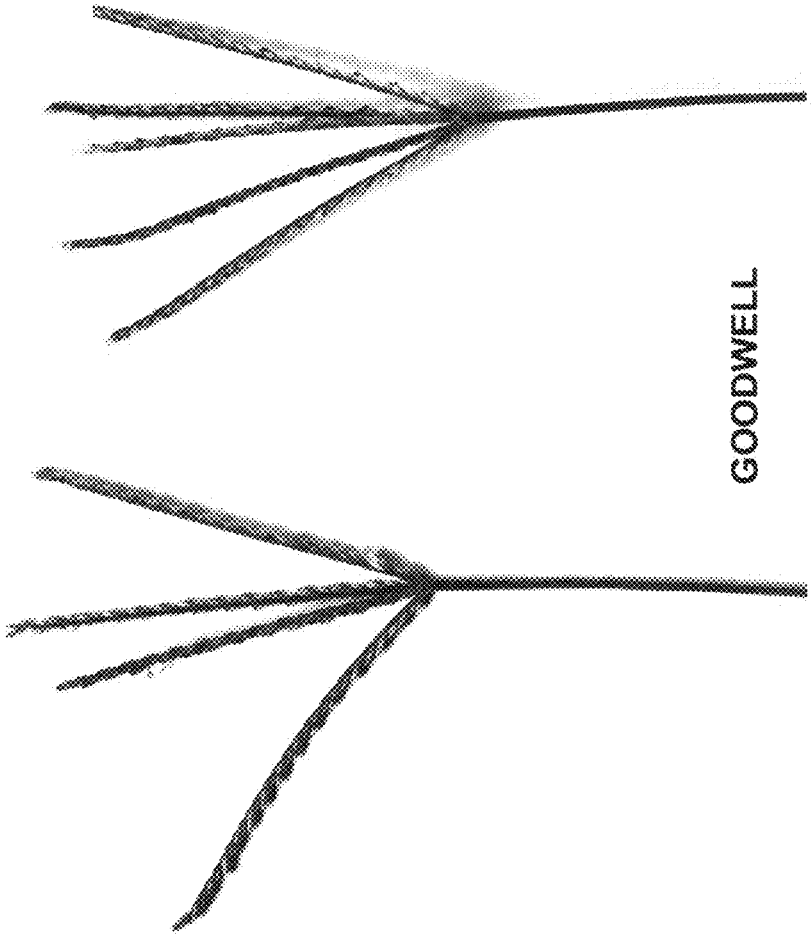
FIG. 4 is an image of two typical 'GOODWELL' inflorescences, one with four racemes and the other with five.
Figure 5:
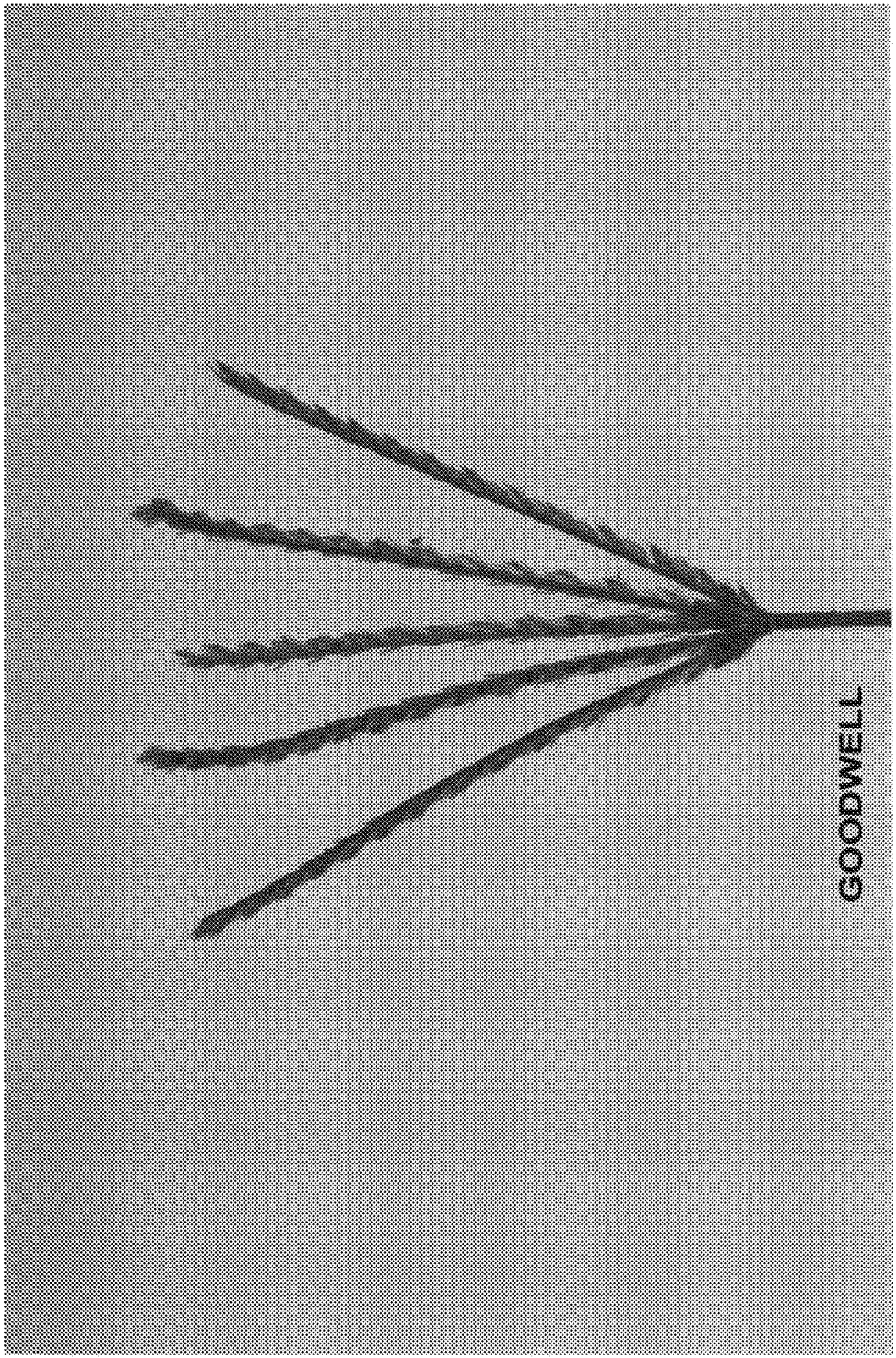
FIG. 5 is a close-up image of the typical inflorescence of a sample 'GOODWELL' plant showing five racemes.
Figure 6:
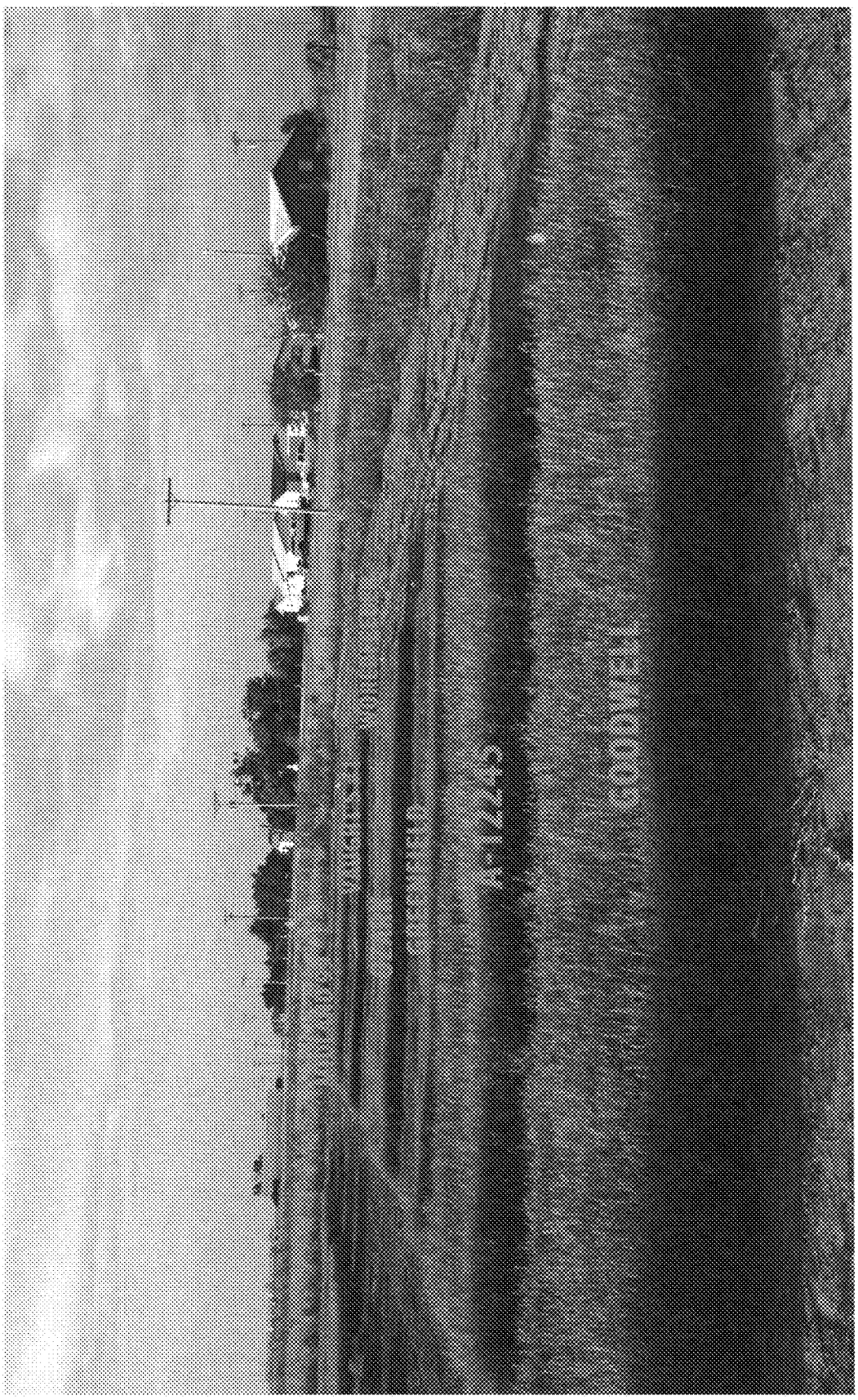
FIG. 6 is an image of 'GOODWELL' growing in a field trial next to A-12245, Sey Greenfield, Ozark, World Feeder, Vaughn's #1, and Midland 99.
Figure 7:
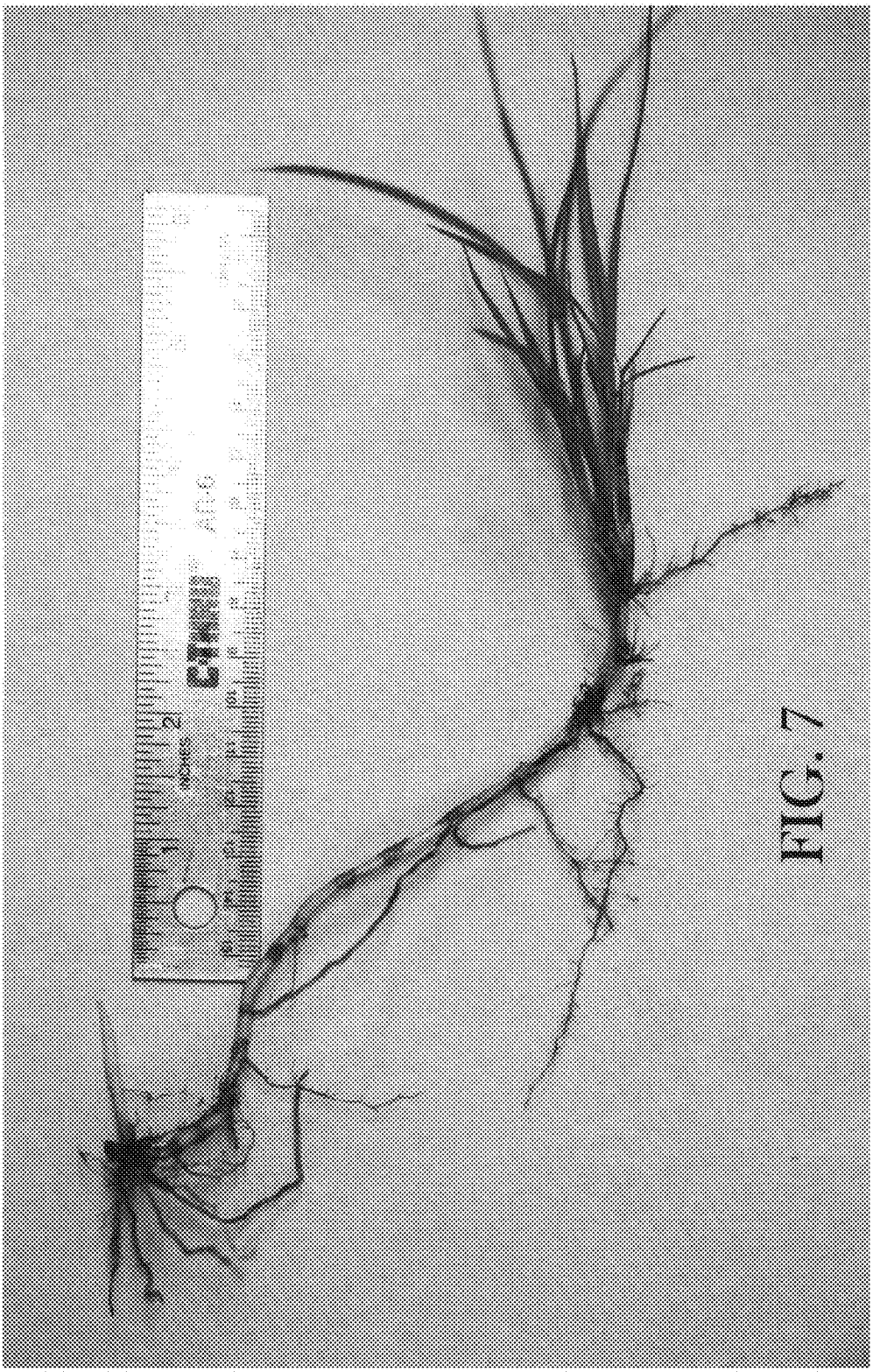
FIG. 7 is an image of 'GOODWELL' next to a ruler for scale, and showing the color of the plant.

Plant height of 'GOODWELL' forage bermudagrass ranges from 41.3 to 43.7 cm. 'GOODWELL' bermudagrass has wider leaf blades than 'Midland 99' or 'Greenfield' (FIG. 2). Both the mean widths of first and second fully expanded leaf blades on stems are 3.3 mm, ranging from 3 to 3.5 mm. Its leaf blade length is from 9.3 to 11.4 cm from the base to tip. Adaxial and abaxial surfaces of leaf blades of 'GOODWELL' bermudagrass are flat, glabrous, and their margins are slightly serrate. Leaf blade tips are sharp but soft. Leaf color is strong yellowish green (FIGS. 1, 2 and 3), rated as RHS 144A or RHS 143B using the color chart of Royal Horticultural Society. Mean diameter of the first and second internodes on shoots is 1.4 and 1.5 mm, respectively. Respective internode length is 3.8 and 4.8 am on the first and second internodes. Color of the stems is the same as of the leaf blades. Ligules of 'GOODWELL' bermudagrass are ciliate about 0.2 mm long and white in color. There are some white hairs just above individual ligules. Inflorescence of 'GOODWELL' consists of 4 or 5 racemes in a single whorl (FIGS. 4 and 5). Racemes are 35 to 40 cm in length. Root systems of 'GOODWELL' bermudagrass are fibrous in shape and brown in color, and major portion of its roots is distributed in top soil from surface to 20 cm deep. 'GOODWELL' bermudagrass has fat rhizomes with length being from 6.5 to 16.3 cm and diameter from 2.9 to 3.9 mm. Color of 'GOODWELL' bermudagrass rhizomes is yellowish white or pale yellow according to the color chart of Royal Horticultural Society (FIG. 7).

Seed of 'GOODWELL' bermudagrass is not well characterized as the grass is primarily vegetatively propagated. 'GOODWELL' bermudagrass was first asexually reproduced in Stillwater, Okla. Sprigs containing rhizomes, or shoots or both are used in reproduction.

TABLE 1

Forage yields (tons dry matter/acre) of commercial and experimental bermudagrass varieties in Test 1997-1, Oklahoma Panhandle Research and Extension Center, Goodwell OK. 1998-2003.

| | Harvest Year | | | |
|---|---|---|---|---|
| Variety | 1998 4-cuts | 1999 4-cuts | 2000 4-cuts | 2001 4-cuts |
| Commercial Varieties - Available for Farm Use | | | | |
| Ozark | 11.84* | 8.00* | 9.94* | 14.53* |
| Midland 99 | 10.16 | 7.60 | 8.53 | 13.00 |
| Hardie | 12.99** | 8.03* | 7.98 | 13.21 |
| Midland | 8.64 | 5.32 | 7.47 | 11.85 |
| Guymon | 9.65 | 4.49 | 5.51 | 11.16 |
| Tifton 44 | 9.23 | 5.48 | 6.98 | 10.39 |
| Wrangler | 10.00 | 4.59 | 5.55 | 10.25 |
| Quickstand | 9.86 | 5.77 | 6.04 | 10.76 |
| Greenfield | 8.91 | 4.18 | 5.24 | 9.73 |
| Experimental Varieties - Not Available for Farm Use | | | | |
| ERS 94X 2-8 | 11.65* | 8.99* | 10.29** | 13.10 |
| 'GOODWELL' | 11.93* | 8.60* | 8.86 | 16.07* |
| LCB 84X 19-16 | 11.59* | 9.74** | 8.51 | 16.24** |
| CD 90160 | 11.75* | 6.85 | 7.56 | 13.30 |
| ERS 94X 13-9 | 9.48 | 6.45 | 7.95 | 13.00 |

TABLE 1-continued

Forage yields (tons dry matter/acre) of commercial and experimental bermudagrass varieties in Test 1997-1, Oklahoma Panhandle Research and Extension Center, Goodwell OK. 1998-2003.

| | | | | |
|---|---|---|---|---|
| SCRS-C | 10.61 | 5.85 | 7.39 | 11.43 |
| ERS 94X 5-12 | 9.23 | 5.57 | 6.31 | 11.10 |
| ERS-C | 8.82 | 4.76 | 5.50 | 9.75 |
| A-12199 | 7.61 | 5.03 | 5.20 | 9.95 |
| ERS 94X 6-13 | 8.08 | 5.07 | 6.13 | 7.69 |
| Mean | 10.11 | 6.33 | 7.21 | 11.91 |
| CV (%) | 16 | 20 | 11 | 15 |
| 5% LSD | 2.34 | 1.77 | 1.09 | 2.60 |

| | Harvest Year | | |
|---|---|---|---|
| Variety | 2002 4-cuts | 2003 4-cuts | 6-yr Mean |
| Commercial Varieties - Available for Farm Use | | | |
| Ozark | 13.25* | 15.10* | 12.11* |
| Midland 99 | 12.86 | 13.48 | 10.94 |
| Hardie | 10.94 | 11.82 | 10.83 |
| Midland | 12.06 | 12.66 | 9.66 |
| Guymon | 11.60 | 12.20 | 9.23 |
| Tifton 44 | 11.00 | 12.34 | 9.10 |
| Wrangler | 11.76 | 11.66 | 8.97 |
| Quickstand | 9.17 | 10.74 | 8.72 |
| Greenfield | 10.86 | 13.15 | 8.68 |
| Experimental Varieties - Not Available for Farm Use | | | |
| ERS 94X 2-8 | 14.80** | 15.97** | 12.46** |
| 'GOODWELL' | 14.51* | 14.49* | 12.41* |
| LCB 84X 19-16 | 13.89* | 14.02* | 12.33* |
| CD 90160 | 13.67* | 13.35 | 11.08 |
| ERS 94X 13-9 | 13.30* | 15.53* | 10.95 |
| SCRS-C | 10.98 | 11.93 | 9.70 |
| ERS 94X 5-12 | 12.29 | 13.57 | 9.66 |
| ERS-C | 11.00 | 13.14 | 8.83 |
| A-12199 | 9.94 | 11.53 | 8.21 |
| ERS 94X 6-13 | 9.04 | 11.28 | 7.88 |
| Mean | 11.94 | 13.05 | 10.09 |
| CV (%) | 13 | 13 | 15 |
| 5% LSD | 2.14 | 2.39 | 0.85 |

**Highest numerical value in column.

*Not significantly different from the highest numerical value in the column based on 5% LSD.

TABLE 2

Forage yields of bermudagrass varieties in Test 2003-1, Goodwell, OK. 2004-2006.

| | Year | | | |
|---|---|---|---|---|
| Variety | 2004 3-Cuts | 2005 4-Cuts | 2006 3-Cuts | Mean |
| | Dry tons/acre | | | |
| 'GOODWELL' | 11.56** | 12.28* | 13.75** | 12.53** |
| Ozark | 10.48* | 12.66** | 13.22* | 12.12* |
| Midland 99 | 10.32* | 10.12 | 12.63* | 11.02 |
| A-12245 | 9.85* | 10.82* | 11.54* | 10.74 |
| Tifton 44 | 10.15* | 10.25 | 11.69* | 10.69 |
| Vaughn's #1 | 8.99 | 9.22 | 8.89 | 9.03 |
| World Feeder | 8.70 | 7.87 | 8.82 | 8.46 |
| Seay | 8.90 | 7.14 | 7.51 | 7.85 |
| Greenfield | | | | |
| Shrimplin | 5.71 | 6.27 | 7.65 | 6.54 |
| Mean | 9.41 | 9.63 | 10.63 | 9.89 |
| CV (%) | 15.05 | 16.77 | 18.20 | 16.89 |
| 5% LSD | 2.07 | 2.36 | 2.82 | 1.36 |

TABLE 3

Forage yields (tons dry matter/acre) of commercial and experimental bermudagrass varieties in Test 98-1, Haskell, OK.

| Varieties | 1999 4-Cuts | 2000 4-Cuts | 2001 3-Cuts | 2002 4-Cuts | 4-Yr Mean |
|---|---|---|---|---|---|
| Commercial Varieties—Available for Farm Use | | | | | |
| Midland 99 | 9.03* | 8.47 | 7.38** | 8.73 | 8.40* |
| Tifton 44 | 7.57 | 7.93 | 5.65 | 7.82 | 7.24 |
| Greenfield | 6.52 | 5.65 | 3.69 | 6.10 | 5.49 |
| Experimental Varieties—Not Available for Farm Use | | | | | |
| ERS 94X 2-8 | 10.24** | 9.82** | 5.99 | 7.91 | 8.49** |
| LCB 84X 19-16 | 8.71 | 9.16* | 7.11* | 8.56 | 8.38* |
| ERS 94X 13-9 | 7.09 | 7.93 | 6.38 | 7.95 | 7.33 |
| 'GOOD-WELL' | 8.70 | 7.51 | 5.59 | 6.76 | 7.14 |
| ERS 94X 5-12 | 7.26 | 7.28 | 4.75 | 7.61 | 6.72 |
| ERS 94X 6-13 | 7.76 | 7.62 | 5.16 | 6.11 | 6.66 |
| SCRS-C | 6.83 | 7.17 | 5.79 | 7.66 | 5.40 |
| ERS-C | 5.78 | 5.93 | 3.43 | 6.46 | 5.40 |
| A12199 | 5.23 | 5.95 | 3.71 | 6.00 | 5.22 |
| Mean | 7.56 | 7.53 | 5.38 | 7.30 | 6.94 |
| CV(%) | 12.7 | 8.7 | 12.5 | 9.0 | 10.6 |
| 5% LSD | 1.38 | 0.94 | 0.97 | 0.94 | 0.51 |

**Highest numerical value in column

*Not significantly different from the highest numerical value in the column based on 5% LSD

TABLE 4

Forage yields (tons dry matter/acre) of commercial and experimental bermudagrass varieties in Test 2001-1, Haskell, OK. 2002-2004.

| Variety | Year 2002 4-cuts | 2003 4-cuts | 2004 3-cuts | Mean |
|---|---|---|---|---|
| Commercial Varieties—Available for Farm Use | | | | |
| Ozark | 11.71** | 10.80* | 10.62** | 11.04** |
| Midland 99 | 11.49* | 10.32 | 10.54* | 10.78* |
| Tifton 44 | 10.90* | 10.22 | 10.35* | 10.49 |
| Experimental Varieties—Not Available for Farm Use | | | | |
| A-12245 | 11.44* | 11.44** | 9.97* | 10.95* |
| ERS16S-4 | 10.97* | 11.10* | 9.61 | 10.56* |
| ERS16S-10 | 11.31* | 9.84 | 9.65 | 10.27 |
| A-12246 | 10.51 | 9.38 | 10.51* | 10.13 |
| ERS16S-2 | 10.61 | 10.23 | 9.37 | 10.07 |
| ERS16S-3 | 9.89 | 9.44 | 9.90 | 9.74 |
| ERS16S-7 | 10.89 | 9.06 | 9.23 | 9.73 |
| ERS16S-9 | 10.62 | 9.97 | 8.45 | 9.68 |
| ERS16S-6 | 10.20 | 9.15 | 9.12 | 9.49 |
| ERS16S-1 | 9.73 | 9.10 | 8.79 | 9.21 |
| ERS16S-8 | 9.29 | 8.48 | 9.45 | 9.08 |
| 'GOODWELL' | 9.61 | 9.68 | 7.70 | 8.99 |
| A-12244 | 9.03 | 7.53 | 9.32 | 8.63 |
| ERS16S-5 | 8.13 | 8.01 | 8.18 | 8.11 |
| Mean | 10.37 | 9.63 | 9.46 | 9.82 |
| CV (%) | 6.89 | 5.95 | 5.17 | 6.10 |
| 5% LSD | 1.02 | 0.81 | 0.69 | 0.48 |

**Highest numerical value in column

*Not significantly different from the highest numerical value in the column based on 5% LSD

TABLE 5

Forage yields (tons dry matter/acre) of commercial and experimental bermudagrass varieties in Test 98-2, Chickasha, OK. 1999-2002.

| Variety | Harvest Year 1999 4-Cuts | 2000 4-Cuts | 2001 4-Cuts | 2002 4-Cuts | 4-Yr Mean |
|---|---|---|---|---|---|
| Commercial Varieties—Available for Farm Use | | | | | |
| Midland 99 | 13.11* | 10.97* | 9.28** | 9.14** | 10.62** |
| Tifton 44 | 12.03 | 12.26** | 7.65 | 8.45* | 10.10* |
| Greenfield | 8.91 | 6.73 | 4.04 | 5.52 | 6..30 |
| Experimental Varieties—Not Available for Farm Use | | | | | |
| ERS 94X 2-8 | 14.21** | 10.31* | 8.68* | 6.80 | 10.00* |
| LCB 84X 19-16 | 11.72 | 10.10* | 8.41* | 7.92 | 9.54 |
| ERS 94X 13-9 | 10.95 | 10.36* | 8.53* | 8.02 | 9.46 |
| SCRS-C | 11.69 | 10.40* | 7.35 | 7.26 | 9.17 |
| 'GOOD-WELL' | 13.00* | 7.46 | 6.08 | 6.82 | 8.34 |
| ERS 94X 6-13 | 10.43 | 8.90 | 6.20 | 4.99 | 7.63 |
| A12199 | 8.56 | 7.21 | 6.03 | 6.15 | 6.98 |
| ERS 94X 5-12 | 9.01 | 6.82 | 5.72 | 6.02 | 6.89 |
| ERS-C | 8.81 | 4.98 | 3.32 | 4.32 | 5.36 |
| Mean | 11.03 | 8.87 | 6.77 | 6.78 | 8.37 |
| CV (%) | 12.9 | 18.0 | 14.3 | 18.3 | 15.7 |
| 5% LSD | 2.05 | 2.30 | 1.39 | 1.79 | 0.92 |

**Highest numerical value in column

*Not significantly different from the highest numerical value in the column based on 5%

TABLE 6

Forage yields (tons dry matter/acre) of commercial and experimental bermudagrass varieties in Test 2001-2, South Central Research Station, Chickasha, OK. 2002-2005.

| Variety | Harvest Year 2002 4 cuts | 2003 4 cuts | 2004 3 cuts | 2005 2 cuts | Mean[1] 2002-2005 | 2002-2005 |
|---|---|---|---|---|---|---|
| | Tons DM/acre | | | | | |
| Midland 99 | 10.97* | 10.91* | 10.77** | 7.04* | 9.92* | 9.57** |
| Ozark[1] | — | 10.36* | 10.06* | 7.35** | — | 9.26* |
| Tifton 44 | 11.72* | 10.19* | 9.78* | 5.17 | 9.26 | 8.45 |
| A12246 | 12.04** | 10.95* | 10.74* | 6.50* | 10.06** | 9.40* |
| A12245 | 11.82* | 11.05* | 10.15* | 5.61 | 9.66* | 8.94* |
| ERS16S 03 | 11.44* | 11.22** | 9.54* | 5.92 | 9.53* | 8.89* |
| ERS16S 04 | 12.44* | 10.14* | 9.20 | 5.98 | 9.44 | 8.44 |
| ERS16S 08 | 9.98 | 9.67 | 9.10 | 6.18 | 8.73 | 8.31 |
| ERS16S 01 | 10.37 | 9.24 | 9.08 | 4.74 | 8.36 | 7.69 |
| 'GOOD WELL' | 10.08 | 8.74 | 8.91 | 4.80 | 8.13 | 7.48 |
| A12244 | 9.73 | 8.30 | 7.86 | 4.56 | 7.61 | 6.91 |
| ERS16S 05 | 9.79 | 9.05 | 7.47 | 3.89 | 7.55 | 6.80 |
| Mean | 10.94 | 9.98 | 9.40 | 5.64 | 8.93 | 8.34 |
| 5% LSD | 1.30 | 1.49 | 1.25 | 1.01 | 0.59 | 0.71 |
| CV (%) | 8.21 | 10.36 | 9.22 | 12.45 | 9.92 | 10.52 |

[1]Ozark yields were not measured in 2002 due to herbicide injury. Ozark plots had recovered by 2003. Plots received 300 lbs. N/acre/yr applied in three equal applications

TABLE 7

Forage yields of bermudagrass varieties and experimental lines at Mound Valley, KS. 1993-1995.

| Entry | Year 1993 | Year 1994 | Year 1995 | 3-Yr Mean |
|---|---|---|---|---|
| | Tons/acre 12% moisture | | | |
| 74X 11-2 | 5.91 | 9.54 | 7.81 | 7.75 |
| 'GOODWELL' | 6.31 | 8.18 | 6.28 | 6.92 |
| LCB 84X 19-16 | 6.05 | 8.36 | 6.04 | 6.82 |
| Ozark | 4.60 | 8.10 | 7.73 | 6.69 |
| LCB 84X 15-49 | 6.04 | 8.01 | 5.92 | 6.65 |
| Hardie | 5.97 | 7.85 | 6.04 | 6.62 |
| 74X 12-12 | 6.12 | 7.22 | 6.52 | 6.62 |
| LCB 84X 9-45 | 6.38 | 7.52 | 5.70 | 6.53 |
| LCB 84X 19-31 | 5.74 | 7.41 | 5.96 | 6.37 |
| Tifton 44 | 5.23 | 7.05 | 5.79 | 6.02 |
| LCB 84X 14-31 | 5.88 | 6.99 | 4.58 | 5.82 |
| LCB 84X 19-23 | 5.54 | 6.52 | 4.75 | 5.60 |
| LCB 84X 12-28 | 5.94 | 6.04 | 4.22 | 5.40 |
| LCB 84X 15-26 | 5.10 | 5.16 | 5.18 | 5.14 |
| Midland | 4.40 | 5.88 | 4.86 | 5.05 |
| LCB 84X 21-57 | 5.24 | 4.25 | 4.74 | 4.74 |
| LCB 84X 18-62 | 4.62 | 4.88 | 4.43 | 4.64 |
| Greenfield | 4.54 | 4.28 | 4.81 | 4.54 |
| World Feeder | 4.11 | 4.30 | 4.44 | 4.28 |
| LCB 84X 16-55 | 4.28 | 3.86 | 3.88 | 4.00 |
| Mean | 5.40 | 6.57 | 5.45 | 5.81 |
| 5% LSD | 0.59 | 0.79 | 0.82 | |

TABLE 8

Mean neutral detergent fiber (NDF), acid detergent fiber (ADF), acid detergent lignin (ADL), crude protein (CP), and in vitro digestible dry matter (IVDMD) of Midland, Tifton 44, and LCB 84X 16-66 bermudagrass cultivars. Stillwater, OK, 1986-87.

| Cultivar | NDF | ADF | ADL | CP | IVDMD |
|---|---|---|---|---|---|
| | Quality trait | | | | |
| | | | $g\ kg^{-1}$ | | |
| 'GOODWELL' | 720 | 342 | 38 | 135 | 604 |
| Tifton 44 | 762 | 334 | 38 | 121 | 553 |
| Midland | 725 | 331 | 40 | 138 | 553 |

Values are means of six sampling dates (Jun. 17, 1986, Jul. 17, 1986, Aug. 22, 1986, Jun. 25, 1987, Aug. 19, 1987, Oct. 5, 1987). Plots were unreplicated.

We claim:

1. A bermudagrass plant substantially as described and illustrated in the specification herein.

* * * * *